US00PP25574P3

(12) United States Plant Patent
Whitaker et al.

(10) Patent No.: US PP25,574 P3
(45) Date of Patent: May 26, 2015

(54) STRAWBERRY PLANT NAMED 'FLORIDA127'

(50) Latin Name: ***Fragaria×ananassa* Duchesne**
Varietal Denomination: Florida127

(71) Applicant: Florida Foundation Seed Producers, Inc., Marianna, FL (US)

(72) Inventors: Vance M. Whitaker, Brandon, FL (US); Craig K. Chandler, Tampa, FL (US)

(73) Assignee: Florida Foundation Seed Producers, Inc., Marianna, FL (US)

( * ) Notice: Subject to any disclaimer, the term of this patent is extended or adjusted under 35 U.S.C. 154(b) by 175 days.

(21) Appl. No.: 13/986,697

(22) Filed: May 24, 2013

(65) Prior Publication Data

US 2014/0359905 P1 Dec. 4, 2014

(51) Int. Cl.
*A01H 5/00* (2006.01)

(52) U.S. Cl.
USPC ..... Plt./208

(58) Field of Classification Search
USPC ..... Plt./208
See application file for complete search history.

(56) References Cited

U.S. PATENT DOCUMENTS

| | | | |
|---|---|---|---|
| PP14,739 | P2 | 4/2004 | Chandler |
| PP20,363 | P2 | 9/2009 | Chandler |
| PP23,042 | P3 | 9/2012 | Chandler |

*Primary Examiner* — Annette Para
(74) *Attorney, Agent, or Firm* — Dentons US LLP

(57) ABSTRACT

A new and distinct variety of strawberry (*Fragaria×ananassa*), which originated from seed produced by a hand-pollinated cross between 'FL 05-107' and 'FL 02-58'. The new strawberry, named 'Florida127', is distinguished by its ability to produce consistently high yields of large and moderately firm, brightly colored fruit that are exceptionally sweet in flavor when grown in west central Florida or other areas that have a subtropical climate similar to that of west central Florida.

2 Drawing Sheets

Latin name of the genus and species of the plant claimed: *Fragaria×ananassa* Duchesne.

Variety denomination: 'Florida127'.

BACKGROUND OF THE INVENTION

The present invention relates to a new and distinct variety of strawberry (*Fragaria×ananassa* Duchesne) plant named 'Florida127'. This new strawberry plant is distinguished by its ability to produce high early and total yields of fruit that are exceptionally and consistently large and sweetly flavored when grown in west central Florida. Asexual propagation was performed at Balm, Fla. where the selection was made and plants were tested. Contrast is made to 'Strawberry Festival' (U.S. Plant Pat. No. 14,739) and 'Florida Radiance' (U.S. Plant Pat. No. 20,363), currently the dominant varieties in Hillsborough County, Fla., for reliable description. This new variety is a promising candidate for commercial success because it produces very large, brightly colored, and easy-to-harvest fruit that are moderately firm and highly flavorful during the entire Florida market window.

This strawberry plant (genotype) originated in a strawberry breeding plot in Balm, Fla. The seed parent was 'FL 05-107' (U.S. Plant Pat. No. 23,042), a strawberry variety with high early-season yield potential, compact plant habit, and very firm fruit. The pollen parent was FL 02-58, an unreleased breeding selection with the ability to produce large fruit with excellent flavor. The seeds resulting from the controlled hybridization were germinated in a greenhouse, and the resulting seedlings were planted and allowed to produce daughter plants by asexual propagation (i.e. by runners). Four daughter plants from each seedling were transplanted to raised beds, where they fruited. 'Florida127' strawberry (as represented by four daughter plants from the original seedling) exhibited high yields and large fruit size, and therefore was selected for further evaluation. 'Florida127' was selection number 127 in the 2009-2010 stage 1 trial, and thus was given the breeding trial designation of FL 09-127. 'Florida127' has been asexually propagated annually by runners, and further test plantings have established that the vegetative and fruit characteristics of the propagules are identical to the initial daughter plants.

SUMMARY OF THE INVENTION

'Florida127', when grown in a subtropical fall and winter climate, is set apart from all other strawberry plants by a combination of the following characteristics: moderately compact growth habit; ease of harvest; and very steady but high yield of fruit that are consistently large in size, bright red, moderately firm and sweetly flavorful.

BRIEF DESCRIPTION OF THE DRAWINGS

The accompanying photographs show a typical specimen of a 5-month-old plant and fruit as seen in February, 2012, in west central Florida.

DETAILED BOTANICAL DESCRIPTION

Figure 1:
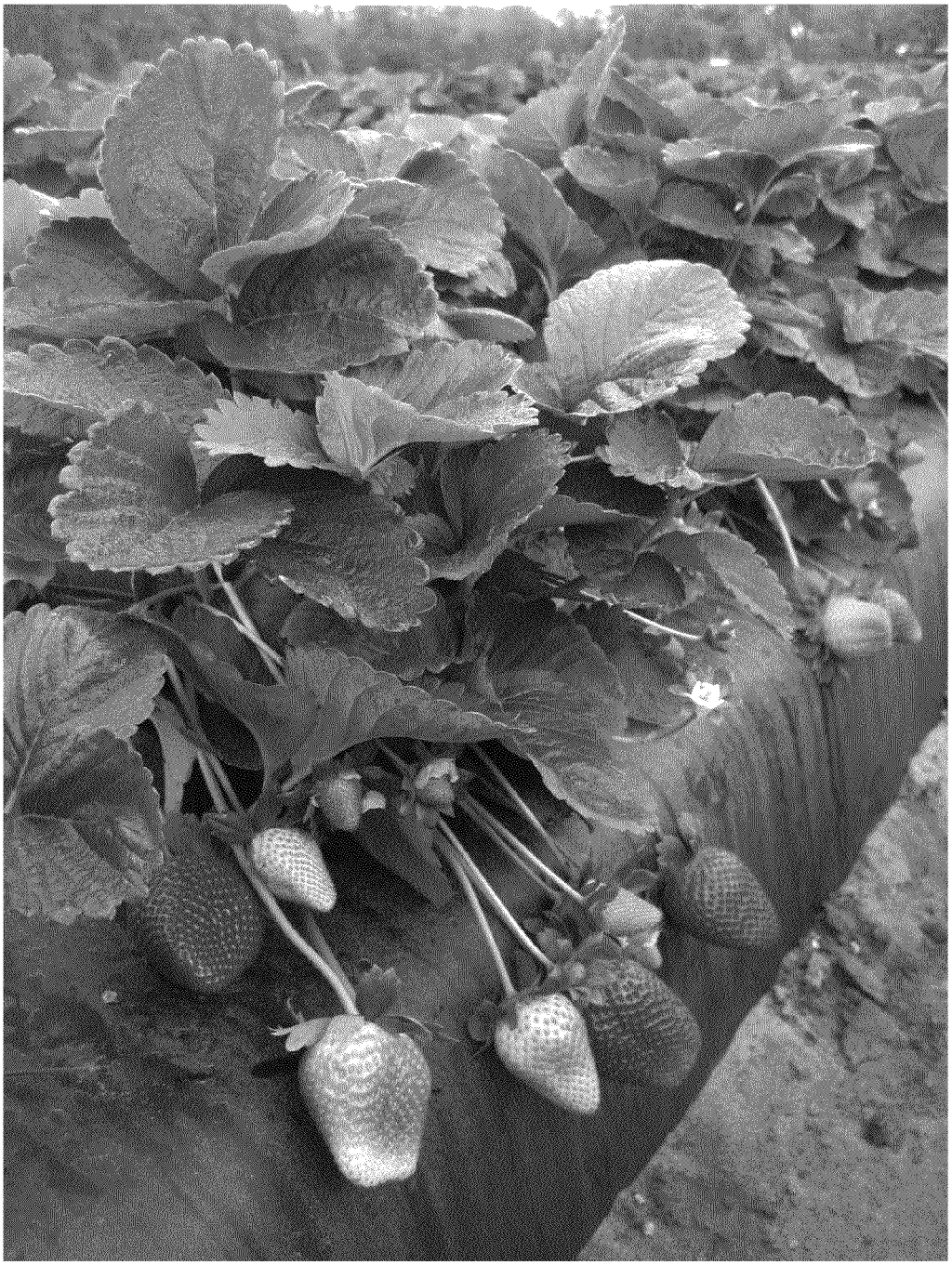
FIG. 1. Shows whole plants, including leaves, inflorescences, and fruit at varying stages of ripeness.
Figure 2:
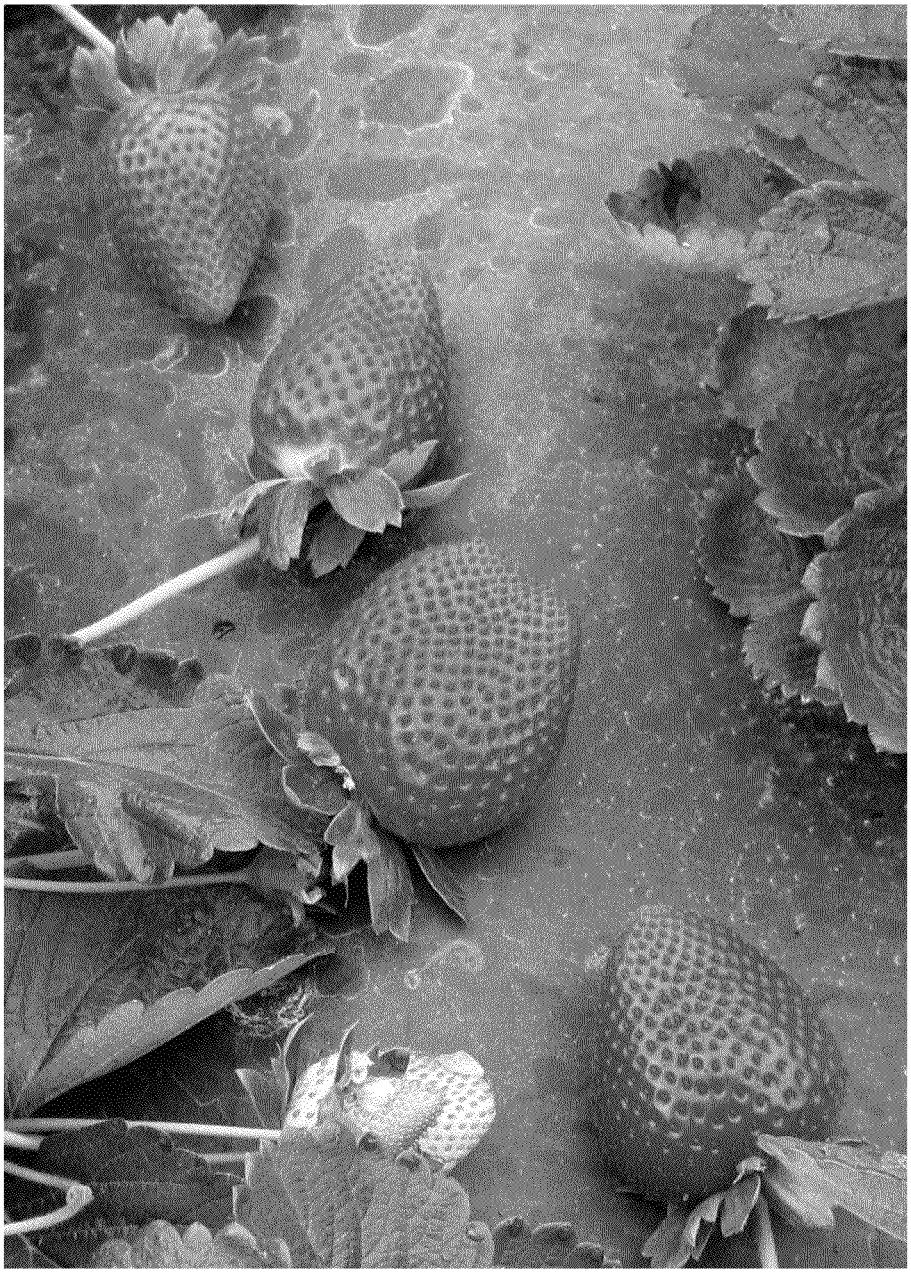
FIG. 2. Shows a close-up of ripe fruit.

The following botanical description is that of mature plants of the claimed variety grown under the ecological conditions (warm days, cool nights) prevailing in Balm, Fla., in March. Colors are objectively described using the L*a*b* color scale with a colorimeter.

Phenotypic description of *Fragaria×ananassa* Duchesne 'Florida127'.

Plant:

*Average height.*—26 cm.

*Average width.*—28 cm.

*Growth habit.*—Moderately compact, semi-erect plants that are not overly dense.

*Number of crowns/plant.*—4 to 7 depending on seasonal conditions.

*Vigor.*—Medium.

Leaf:

*Overall description.*—Pinnately compound with three leaflets.

Petiole:

*Average length.*—17.5 cm.

*Average diameter.*—3 mm.

*Pubescence.*—Light to medium.

*Pubescence density.*—Moderate to sparse.

*Pose of hairs.*—Ascending.

*Texture.*—Smooth.

*Anthocyanin.*—Absent.

*Color.*—Medium green (L*=34.3, a*=−10.9, b*=13.6).

Petiolule:

*Length.*—Terminal leaflet, 9 mm; lateral leaflets, 4 mm.

*Diameter.*—2 mm.

Stipule:

*Length.*—30 mm.

*Width.*—17 mm along base of petiole attachment.

*Anthocyanin.*—Slight.

Terminal leaflet:

*Average length.*—78 mm.

*Average breadth.*—68 mm.

*Length/width ratio.*—1.15.

*Shape in cross section.*—concave.

*Color, upper surface.*—Medium gray-green (L*=34.7, a*=−10.5, b*=13.1).

*Glossiness.*—Slight gloss.

*Base shape.*—Cuneate to slightly rounded.

*Apex descriptor.*—Rounded.

*Pubescence density.*—Sparse.

*Texture.*—Moderately smooth.

*Venation pattern.*—Pinnate.

Secondary leaflets:

*Average length.*—70 mm.

*Average breadth.*—68 mm.

*Length/width ratio.*—1.03.

*Shape in cross section.*—Concave.

*Color, upper surface.*—Medium gray-green (L*=34.7, a*=−10.5, b*=13.1).

*Glossiness.*—Slight gloss.

*Base shape.*—Oblique rounded.

*Apex descriptor.*—Obtuse.

*Pubescence density.*—Sparse.

*Texture.*—Moderately smooth.

*Venation pattern.*—Pinnate.

Leaflet margins: Crenate, with an average of 22 serrations per terminal leaflet and 17 per secondary leaflet.

Stolons:

*Number of daughter plants.*—25-40, depending on environmental conditions.

*Anthocyanin.*—Variable; absent to moderate.

*Thickness.*—2-3 mm.

*Pubescence.*—Very sparse, nearly glabrous.

Inflorescence:

*Time of flowering.*—Short-day but exhibits partial remontancy.

*Position relative to canopy.*—Flowers open at or below canopy height.

*Branching of the inflorescence.*—At or very close to the crown.

Petals:

*Number.*—6 to 8.

*Length.*—11 mm.

*Width.*—10 mm.

*Mean diameter of the corolla* (*i.e. the petals collectively*).—32 mm.

*Number of stamens.*—Average of 27.

Calyx:

*Diameter of calyx relative to corolla.*—Same.

*Color.*—Medium green (L*=35.3, a*=−11.3, b*=13.8).

Pedicels:

*Attached to mature primary fruit.*—12.5 to 16.0 cm long, depending on time of season. At peak production, the plant will have several crowns, each producing a truss, and each truss will have 3-7 pedicels. Inforescences branch very close to the crown, rendering the peduncle rarely visible.

Fruit:

*Mean fruit weight.*—Greater than 'Strawberry Festival' and greater than or equal to that of 'Florida Radiance' (Table 1).

*Shape.*—Medium conical to cordate in shape.

*Weight, primary fruit.*—35-45 g.

*Weight, secondary and tertiary fruit.*—15-35 g.

*Fruit flavor.*—Sweet, partly due to the consistently high soluble solids content (SSC) of the fruit and moderate acidity (Table 2).

*Fruit cavity.*—Occasional on primary fruit but rare on secondary or tertiary fruit.

*Achenes.*—Slightly sunken, giving the fruit a smooth appearance.

*External fruit color.*—Glossy bright red (a*=38.9).

*Internal fruit color.*—Medium red (a*=24.0).

*Evenness of color.*—Even to slightly uneven during cold and cloudy conditions.

*Flesh and skin firmness at full ripe stage.*—Moderately firm.

*Rain damage.*—'Florida127' is less resistant to cracking of the fruit by rain than 'Strawberry Festival' and 'Florida Radiance'.

Total yield: Greater than 'Strawberry Festival' during both the 2011-2012 and 2012-2013 seasons (Table 1). Yield was not different from 'Florida Radiance' during the 2012-13 season, except in January, when the marketable yield of 'Florida127' was significantly greater (Table 1).

Preferred planting period: October 1st to October 15$^{th}$ in west-central Florida.

*Nursery performance.*—'Florida127' is expected to perform well in nursery situations, due to the production of many runners, which results in sturdy, compact daughter plants. This is in contrast to 'Florida Radiance', whose daughter plants have weak petioles that are susceptible to breakage during digging and handling.

Disease resistance: 'Florida127' is moderately susceptible to *Botrytis* fruit rot (caused by *Botrytis cinerea*), similar to 'Florida Radiance'. 'Florida127' is resistant to anthracnose fruit rot (caused by *Colletotrichum acutatum*).

TABLE 1

Performance of three strawberry genotypes during the 2011-12 and 2012-13 seasons in Balm, FL,

| Cultivar | Marketable yield (g/plant) | | | |
|---|---|---|---|---|
| | November | December | January | February |
| 2011-12 | | | | |
| Florida127 | 12.7 a[y] | 103.8 b | 182.5 a | 428.0 a |
| S. Festival | 13.7 a | 129.9 a | 106.6 b | 321.1 b |
| 2012-13 | | | | |
| Florida127 | 3.2 a | 88.7 a | 252.3 a | 298.9 a |
| F. Radiance | 0.5 a | 82.1 a | 198.4 b | 394.4 a |
| S. Festival | 0.0 a | 101.5 a | 133.2 c | 298.5 a |

| Cultivar | Marketable yield (g/plant) | | |
|---|---|---|---|
| | March | Total | Wt/fruit (g)[z] |
| 2011-12 | | | |
| Florida127 | 293.2 a | 1,020.1 a | 25.8 a |
| S. Festival | 112.3 b | 683.6 b | 17.9 b |
| 2012-13 | | | |
| Florida127 | 35.8 a | 678.9 a | 23.8 a |
| F. Radiance | 45.3 a | 720.7 a | 23.7 a |
| S. Festival | 11.0 b | 544.2 b | 18.1 b |

[z]Mean fruit weight was determined by dividing total marketable fruit yield per plot by total marketable fruit number per plot.

[y]Means are based on four replications of 10 plants each. Means separation within columns is by LSD test, $P \leq 0.05$.

TABLE 2

Fruit chemical measures on five dates over two harvest seasons.

| Cultivar | SSC | pH | TA | SSC/TA |
|---|---|---|---|---|
| February 2011 | | | | |
| FL 09-127 | 9.6 a[z] | 3.74 a | 0.788 a | 12.17 a |
| S. Festival | 7.4 b | 3.63 b | 0.838 a | 8.89 b |
| F. Radiance | 6.4 c | 3.66 b | 0.787 a | 8.11 c |
| March 2011 | | | | |
| FL 09-127 | 6.7 a | 3.6 a | 0.864 ab | 7.81 a |
| S. Festival | 7.2 a | 3.6 a | 0.905 a | 7.98 a |
| F. Radiance | 5.6 b | 3.6 a | 0.793 b | 7.07 b |
| January 2012 | | | | |
| FL 09-127 | 9.4 a | 3.8 a | 0.781 b | 12.49 a |
| S. Festival | 8.6 b | 3.6 b | 0.931 a | 9.25 b |
| F. Radiance | 8.8 b | 3.7 a | 0.808 b | 10.98 ab |
| February 2012 | | | | |
| FL 09-127 | 7.3 a | 3.7 a | 0.759 a | 9.63 a |
| S. Festival | 6.1 b | 3.6 b | 0.808 a | 7.60 b |
| F. Radiance | 5.8 b | 3.7 a | 0.721 a | 8.11 b |
| March 2012 | | | | |
| FL 09-127 | 6.9 a | 3.6 a | 0.717 a | 9.67 a |
| S. Festival | 5.6 b | 3.5 b | 0.744 a | 7.49 b |
| F. Radiance | 5.0 b | 3.6 a | 0.689 a | 7.22 b |

[z]Mean separations are within harvest dates and within columns by LSD test, $P \leq 0.05$.

What is claimed is:

1. A new and distinct strawberry plant as illustrated and described herein, characterized by:

(1) a moderately compact plant with long pedicels allowing for ease of harvest;

(2) large fruit size; and (3) high early and total yields of bright red and moderately firm fruit that are sweetly flavored when grown in west central Florida.

* * * * *